United States Patent [19]

Hyon et al.

[11] Patent Number: 4,781,926
[45] Date of Patent: Nov. 1, 1988

[54] TRANSDERMAL THERAPEUTIC COMPOSITION

[75] Inventors: Suong-Hyu Hyon; Yoshito Ikada, both of Uji, Japan

[73] Assignee: Biomaterials Universe, Inc., Osaka, Japan

[21] Appl. No.: 842,187

[22] Filed: Mar. 21, 1986

[30] Foreign Application Priority Data

Mar. 25, 1985 [JP] Japan .................................. 60-60220

[51] Int. Cl.$^4$ ............................................. A61L 15/00
[52] U.S. Cl. ..................................... 424/486; 424/485
[58] Field of Search ................................. 424/485, 486

[56] References Cited

U.S. PATENT DOCUMENTS

| 4,292,303 | 9/1981 | Keith | 424/486 |
| 4,294,820 | 10/1981 | Keith | 424/486 |
| 4,321,252 | 3/1982 | Keith | 424/486 |
| 4,381,772 | 5/1983 | Guistini et al. | 424/486 |
| 4,482,533 | 11/1984 | Keith | 424/486 |
| 4,542,013 | 9/1985 | Keith | 424/486 |
| 4,624,848 | 11/1986 | Lee | 424/486 |
| 4,642,233 | 2/1987 | Urguhart et al. | 424/486 |

Primary Examiner—Thurman K. Page
Assistant Examiner—L. R. Horne
Attorney, Agent, or Firm—Antonelli, Terry & Wands

[57] ABSTRACT

Transdermal dosage compositions are prepared from hydrated poly(vinyl alcohol) gels and pharmacologically active substances without any chemicals such as crosslinking agents and catalysts. Heating process is not involved in the gel preparation. High water contents of the gels enable the stratum corneum to be swollen, resulting in high permeation of drugs through the skin.

7 Claims, No Drawings

TRANSDERMAL THERAPEUTIC COMPOSITION

BACKGROUND OF THE INVENTION

The present invention relates to a transdermal therapeutic composition designed to accelerate drug absorption through the skin and mucous membranes.

Conventional dermal administration forms such as ointments have been used ever since the the nineteenth century for the therapy of bruise, sprain, muscleache, and so on.

Recently new transdermal therapeutic systems which make possible the constant slow release of drugs, have been developed for the therapy of diseases of internal organs besides those of skin and trauma using the drugs which are quite effective even in a small amount and excellent in transdermal permeation. The well-known examples of the clinical use are the transdermal therapeutic system with nitroglycerin for the therapy of angina pectoris and with scopolamine for motion sickness. However, as these drugs permeate the skin too rapidly to invoke side-effects, such membranes as silicone and ethylene-vinyl acetate copolymers have been employed to retard and control the absorption rate of the drugs.

In addition to the two drugs, many other drugs have been tried for the transdermal administration; the examples are an unguenta form of indomethacine as an antiinflammatory agent (Japanese Unexamined Patent Publication (Tokkyo Kokai) No. 81616/1978) and a cataplasmata form of indomethacine (Japanese Unexamined Patent Publication (Tokkyo Kokai) No. 62013/1980). Drugs for hypertension and depression as well as adrenal cortical hormones and progesterones have been also attempted for the transdermal therapeutic system. Contrary to nitroglycerin, these pharmacologically active substances have very poor transdermal permeability, so that some new means are required for enhancement of the skin absorption.

The widely attempted method for this purpose is to make the stratum corneum to become much swollen by humidifying the skin or to utilize absorption enhancers for the skin absorption. In order to swell the stratum corneum with water, it is necessary to increase the water content of the transdermal dosage form inself. Based on this principle, a dosage form of indomethacine with a high water content has been developed (Japanese Examined Patent Publication (Tokkyo Kokoku) No. 27248/1983). This is prepared from hydrogel which consists of poly(acrylic acid) crosslinked with an epoxy-type crosslinking agent. However, this matrix polymer has a problem for clinical use because of the toxicity of the crosslinking agent employed.

An object of the invention is to prepare transdermal dosage forms which are capable of making the stratum corneum much swollen in order to constantly release the pharmacologically active substances included in the forms without exerting side-effects to the body.

SUMMARY OF THE INVENTION

According to the present invention, there can be provided a transdermal therapeutic composition which comprises hydrated gels of poly(vinyl alcohol) containing pharmacologically active substances, or pharmacologically active substances and absorption enhancers for the active substances and/or tackifiers.

DETAILED DESCRIPTION

The hydrated gels of poly(vinyl alcohol) (hereinafter referred to as "hydrated PVA gels") employed as the base matrix for the dosage forms in the invention have a porous and three-dimensional network structure with high mechanical strengths and high water contents. The final dosage forms are fabricated by forming the PVA gels in the presence of pharmacologically active substances alone, or a mixture with other additives.

The dosage forms comprising the hydrated PVA gel can be prepared by various methods. The typical one is to freeze aqueous solutions of PVA containing the pharmacologically active substances and, if necessary, the additives below the freezing point to yield a phase structure separated into PVA phases and ice phases, followed by crystallization of the PVA phases above the freezing point.

The degree of saponification of PVA to be used for the dosage form preparation should be higher than 95% by mole, preferably 97% by mole and most preferably higher than 99% by mole. If PVA has a degree of saponification, for instance, lower than 85% by mole, the gels obtained from the PVA exhibit no high mechanical strength. The viscosity-average degree of polymerization of PVA to be used in this method should be higher than 1,000, preferably 1,500. The commercially available PVA with degrees of polymerization ranging from 1,700 to 2,500 is recommended, as the gel strength becomes lower with the decreasing degree of polymerization.

Using PVA of such molecular properties, highly concentrated aqueous solutions are prepared at the PVA concentration which ranges mostly from 10 to 30% by weight. Such highly concentrated solutions can be readily prepared by raising the temperature of the mixture from PVA and water by the use of an autoclave or a high-frequency heater. The addition be made either before or after the preparation of aqueous solutions of PVA.

The PVA solution containing the pharmacologically active substances is cast into a mold of the dosage form, followed by freezing below the freezing point. The temperature for freezing should be low enough for the aqueous solution to be thoroughly frozen, preferably below $-5°$ C. and most preferably below $-20°$ C., because an addition of the absorption enhancer often lowers significantly the freezing point of the PVA solution. Upon freezing, the aqueous solution undergoes microscopic separation into two phases; the ice phase and the PVA phase. It seems that most of the added pharmacologically active substance may be present in the PVA phase, but some of them in the ice phase or in the interfacial phase between the PVA and the ice phase, depending on the nature of the drugs.

The temperature of the frozen, phase-separated solid is raised above the freezing point, preferably to 0° to 10° C. in order to further crystallize the PVA phase. The crystallization is allowed to proceed longer than 10 hr. If this period of time is shorter than 10 hr, the PVA would be crystallized to an insufficient extent, resulting in formation of gels with low mechanical strengths. Defreezing temperatures higher than 10° C. will lead to too high defreezing rates to make the extent of crystallization of PVA lower. As a result, the pharmacologically active substances could not be retained strongly enough inside the gels.

By a series of these processes there can be obtained the PVA gel containing the pharmacologically active substances and possessing both high mechanical strengths and high water contents. It should be pointed out that these gel dosage forms are non-toxic because of no use of any chemicals such as catalyst and crosslinking agent.

The rate of release from the gel and the subsequent skin permeation of the pharmacologically active substances can be widely controlled by changing the concentration of PVA, the pharmacologically active substances, and the absorption enhancer in the gel. The pharmacologically active substances to be added to the PVA gel are not restricted, insofar as they are drugs for therapy and prevention of human or animal diseases. Not only water-soluble but also water-insoluble drugs can be used in any form of liquid, powder, bead, and the like. The formulation amount of the drugs is determined on the basis of the administration purpose, the supply form, the skin permeability, and the like. 0.01 to 500 parts (part by weight, hereinafter the same), most preferably 10 to 50 parts of the drug are added to 100 parts of PVA by weight for the conventional PVA gel dosage forms.

Among the absorption enhancers are, for example, alcohols, esters, ketones, and alkyl sulfoxides, but there is no restriction on the selection. Alcohols include ethyl alcohol, ethylene glycol, diethylene glycol, triethylene glycol, poly(ethylene glycol), propylene glycol, poly(propylene glycol), glycerin, and the like. Esters include ethyl acetate, monoesters from monocarboxylic acids with 4 to 14 carbons and alcohols having 1 to 5 carbon atoms such as ethyl caproate, diesters from dicarboxylic acids having 4 to 10 carbon atoms and alcohols having 1 to 4 carbon atoms such as diisopropyl adipate and diethyl sebacate, and the like. Alkyl sulfoxides include dimethyl sulfoxide, diethyl sulfoxide, and the like. The amount of these absorption enhancers ranges from 0.1 to 1,000% by weight based on the PVA in the hydrated gel. The enhancer exhibits no good effect when added in amounts lower than 0.1% by weight and gives undesirable influences on the gel formation if the added amount surpasses 1,000% by weight. It is often recommended to add to the gels Azone ® and the analogues such as 1-buthyl azacyclopentane-2-one, 1-n-heptyl azacyclopentane-2-one, and other absorption enhancers such as aspirin and salicylic acid.

The tackifiers to be compounded in the PVA gel include PVA with low degrees of saponification, gelatin, starch, hydroxypropyl cellulose, poly(ethylene oxide), poly(vinyl-N-pyrrolidone), acrylic acid copolymers, sodium alginate, and the like. The tackifier amount is 0.1 to 100% by weight based on the PVA in the gel. The tackifier has no good effect when added in amounts lower than 0.1% by weight and gives undesirable influences on the gel formation if the added amount surpasses 100% by weight. The amount to be added is preferably in the range of 10 to 20% by weight.

The shape of the dosage forms of the invention is determined according to the administration purpose, usually film-, sheet-, sponge-, or tape-like.

The present invention is more specifically described and explained by means of the following Examples and Comparative Examples. It is to be understood that the present invention is not limited to the Examples and various changes and modifications may be made in the invention without departing from the spirit and scope thereof.

EXAMPLE 1

A 15% by weight aqueous solution of PVA was prepared from 85 parts of water and 15 parts of PVA with the degree of saponification of 99.5% by mole and the viscosity-average degree of polymerization of 1,700. To 5 g of this solution 200 mg of clonidine hydrochloride (hypertensive drug) was added and poured into a plastic container with a flat bottom. After freezing at $-20°$ C. for 10 hr in a freezer, the mixture was kept at 5° C. for 10 hr in a freezer, the mixture was kept at 5° C. for 10 hr in a refrigerator for defreezing and crystallization of PVA. A hydrated PVA gel sheet of 1 mm in thickness containing the hypertensive drug was obtained by the procedures.

EXAMPLE 2

A hydrated PVA gel sheet of 1 mm in thickness containing the hypertensive drug was prepared by the same procedures as described in Example 1, except that a 20% by weight aqueous solution of PVA was used instead of the 15% by weight solution.

EXAMPLE 3

A hydrated PVA gel sheet of 1 mm in thickness containing the hypertensive drug was prepared by the same procedures as described in Example 1, except that a 20% by weight aqueous solution of PVA was prepared from 80 parts of water, 18 parts of PVA with the degree of saponification of 99.5% by mole and the degree of polymerization of 1,700, and 2 parts of PVA with the degree of saponification of 88% by mole and the degree of polymerization of 500.

EXAMPLE 4

A 15% by weight aqueous solution of PVA was prepared similarly using the same PVA as in Example 1. A solution prepared from 5 ml of ethyl acetate and 0.5 g of isosorbide dinitrate (angina pectori drug) was dispersed into 50 g of the PVA solution. By similar freezing and defreezing process as described in Example 1, a hydrated PVA gel sheet of 1 mm in thickness containing the angina drug was prepared.

EXAMPLE 5

A 15% by weight of aqueous solution of PVA was prepared similarly using the same PVA as in Example 1. A solution prepared from 5 ml of ethyl alcohol and 0.5 g of dicrofenac sodium (anti-inflammatory, analgesic drug) was dispersed into 20 g of the PVA solution. By similar freezing and defreezing process as described in Example 1, a hydrated PVA gel sheet of 1 mm in thickness containing the anti-inflammatory drug was prepared.

EXAMPLE 6

A hydrated PVA gel sheet of 1 mm in thickness containing dicrofenac sodium was prepared by the same procedures described in Example 5 except that 10 ml of ethyl alcohol was used instead of 5 ml of ethyl alcohol.

EXAMPLE 7

A 15% by weight aqueous solution of PVA was prepared similarly using the same PVA as in Example 1. A solution prepared from 4.5 g of ethylene glycol and 0.5 g of indomethacine (anti-inflammatory, analgesic drug) was dispersed into 20 g of the PVA solution. By similar freezing and defreezing process as described in Example 1, a hydrated PVA gel sheet of 1 mm in thickness containing the anti-inflammatory drug was prepared.

EXAMPLE 8

A 15% by weight aqueous solution of PVA was prepared similarly by using the same PVA as in Example 1. 0.5 g of chromiplamin hydrochloride (tricyclic antidepressant) and 0.1 g of Azone ® were admixed to 20 g of the PVA solution. By similar freezing and defreezing process as described in Example 1, a hydrated PVA gel sheet of 1 mm in thickness containing the antidepressant was prepared.

COMPARATIVE EXAMPLE 1

2.5 g of dicrofenac dinitrate was dissolved in the solution obtained by addition of 1 g of carboxyvinyl polymer (Carbopol 940 ®) to the mixture of 50 g of water and 50 g of ethyl alcohol. On addition of 1 g of triethylamine a gel form was obtained.

COMPARATIVE EXAMPLE 2

200 mg of propranol hydrochloride (β-blocker of hypertensive drug) was dissolved in 5 g of 15% by weight aqueous solution of PVA with the degree of saponification of 99.5% by mole and the degree of polymerization of 1,700. On addition of 0.05 g of glutaraldehyde and 0.01 g of 0.1N HCl, a PVA gel form was obtained.

COMPARATIVE EXAMPLE 3

0.5 g of isosorbide dinitrate was dissolved in 20 g of 2-hydroxyethyl methacrylate monomer. To this solution were added 1 g of acrylic acid, 0.5 g of 1,4-butanediol dimethacrylate, 150 mg of benzoyl peroxide, and 0.2 g of N,N-di-methyl-p-toluidine. A gel form was obtained upon polymerization of the monomers.

TEST EXAMPLE 1

Plasters were fabricated by laminating the gel forms prepared in Examples 1 to 8 and Comparative Examples 1 to 3 with a pressure-sensitive adhesive film (ethylenevinyl acetate copolymer/polyester laminate) on one side and with a released paper (polyethylene/aluminium laminate film) on the other side. The dimensional stability of these plasters kept at room temperature for 12 months and the adhesion property of these plasters applied to the back of guinea pigs are shown in Table 1.

TEST EXAMPLE 2

The plasters fabricated in Test Example 1 (2×2 cm) were applied to the back of guinea pigs for 5, 10, and 24 hr, and then the amount of drugs remaining in the gel forms was determined. The amount of drugs absorbed in the body, calculated from the above determination, is shown in Table 2.

TABLE 1

| Plaster | Dimensional stability | Adhesion property |
| --- | --- | --- |
| Example 1 | good | good |
| Example 2 | good | good |
| Example 3 | good | excellent |
| Example 4 | good | good |
| Example 5 | good | good |
| Example 6 | good | good |
| Example 7 | good | good |
| Example 8 | good | good |
| Com. Ex. 1 | not good | good |
| Com. Ex. 2 | not good | good |

TABLE 1-continued

| Plaster | Dimensional stability | Adhesion property |
| --- | --- | --- |
| Com. Ex. 3 | good | not good |

TABLE 2

| Transdermal dosage form | Absorption (%) | | |
| --- | --- | --- | --- |
| | after 5 hr | after 10 hr | after 24 hr |
| Example 1 | 3 | 12 | 25 |
| Example 2 | 2 | 9 | 18 |
| Example 3 | 3 | 11 | 22 |
| Example 4 | 21 | 63 | 96 |
| Example 5 | 9 | 24 | 41 |
| Example 6 | 13 | 30 | 49 |
| Example 7 | 7 | 22 | 37 |
| Example 8 | 11 | 19 | 32 |
| Comp. Ex. 1 | 5 | 16 | 18 |
| Comp. Ex. 2 | 1 | 3 | 7 |
| Comp. Ex. 3 | 4 | 10 | 13 |

As is shown in Table 1, the transdermal administration forms of the present invention are excellent both in the dimensional stability and the adhesion property. Also, as is clear from comparison of the results on Examples 1 to 2 in Table 2, the drug absorption can be controlled by the PVA concentration of the gel. As is clear from comparison of the results on Examples 5 to 8 in Table 2 the drug absorption can be controlled by the use of the absorption enhancers. The result on Example 3 in Table 2 indicates that the adhesive power of the gel forms with the skin can be promoted by the use of tackifiers.

The advantages of the transdermal therapeutic system of the invention are summarized as follows. Insofar as the drugs contained in the gel dosage forms have good stability against water, reduction in pharmacological activity and chemical changes of the drugs do not occur on storage, since neither crosslinking agent nor catalyst are used in the gel preparation and, in addition, heating process is not involved in the preparation. The gel forms give no adverse reaction to the body. The high water contents of the gels result in swelling of the stratum, which leads to enhanced permeation of drugs through the skin. The drugs can be homogeneously distributed in the gel forms, independent of their solubility and shape. The use of absorption enhancers and tackifiers promotes the drug absorption and the drug adhesive power with the skin, respectively.

What we claim is:

1. A transdermal therapuetic article in the form of a film or sheet prepared by freezing an aqueous solution of polyvinyl alcohol containing pharmacologically active substances and pharmacologically acceptable additives at a temperature below −5° C., and then defreezing the frozen solution at a temperature of 0° to 10° C. for at least 10 hours.

2. The article of claim 1, wherein the additives are absorption enhancers for the active substances.

3. The article of claim 1, wherein the additives are tackifiers.

4. The article of claim 2, wherein the absorption enhancers are selected from the group consisting of alcohols, esters, ketones, and alkyl sulfoxides.

5. The article of claim 3, wherein the tackifiers are water-soluble polymers selected from the group consisting of poly(vinyl alcohol) with a low degree of saponification, gelatin, starch, hydroxypropyl cellulose, poly- (ethylene oxide), poly(vinyl-N-pyrrolidone), acrylic acid copolymers, and sodium alginate.

6. The article of claim 1, wherein 0.01 to 500 parts by weight of the pharmacologically active substances are admixed with 100 parts by weight of the poly(vinyl alcohol) and the additives are absorption enhancers for the active substances and are present in an amount of from 0.1 to 1,000% by weight based on the weight of the poly(vinyl alcohol).

7. The article of claim 1, wherein 0.01 to 500 parts by weight of the pharmacologically active substances are admixed with 100 parts by weight of the poly(vinyl alcohol) and the additives are tackifiers for the active substances and are present in an amount of from 0.1 to 10% by weight based on the weight of the poly(vinyl alcohol).

* * * * *